Figure 1:
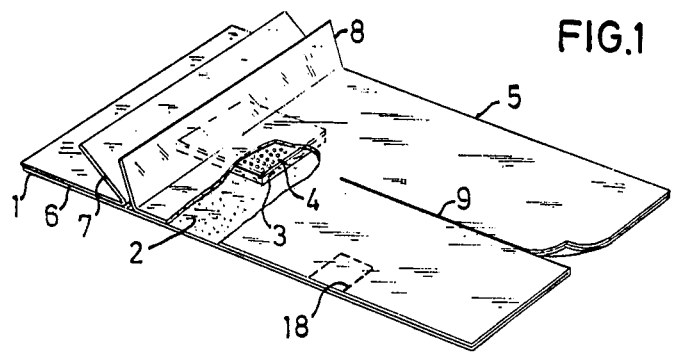

United States Patent [19]
Olson

[11] 4,275,721
[45] Jun. 30, 1981

[54] VEIN CATHETER BANDAGE

[75] Inventor: Karin S. B. Olson, Lund, Sweden

[73] Assignee: Landstingens Inkopscentral Lic, Ekonomisk Forening, Solna, Sweden

[21] Appl. No.: 96,553

[22] Filed: Nov. 21, 1979

[30] Foreign Application Priority Data

Nov. 28, 1978 [SE] Sweden ................ 7812240

[51] Int. Cl.³ .................... A61M 5/00; A61M 25/02
[52] U.S. Cl. ................... 128/133; 128/214 R; 128/DIG. 26
[58] Field of Search ........... 128/214, 214 R, 215, 128/348–351, 132, 133, DIG.26

[56] References Cited

U.S. PATENT DOCUMENTS

| | | | |
|---|---|---|---|
| 2,727,512 | 12/1955 | Muller | 128/133 |
| 3,138,158 | 6/1964 | Gordon et al. | 128/214 R |
| 3,683,911 | 8/1972 | McCormick | 128/214 R |
| 3,722,508 | 3/1973 | Roberts | 128/214 R X |
| 3,834,380 | 9/1974 | Boyd | 128/DIG. 26 |
| 3,918,446 | 11/1975 | Buttaravoli | 128/133 |
| 4,040,427 | 8/1977 | Winnie | 128/348 |
| 4,080,970 | 3/1978 | Miller | 128/350 R |
| 4,122,857 | 10/1978 | Haerr | 128/133 X |
| 4,129,128 | 12/1978 | McFarlane | 128/133 |
| 4,221,215 | 9/1980 | Mandelbaum | 128/DIG. 26 |

*Primary Examiner*—Stephen C. Pellegrino
*Attorney, Agent, or Firm*—Cushman, Darby & Cushman

[57] ABSTRACT

A vein catheter bandage with hose, tubular coupling member, laterally directed wings, stop cock on the coupling member or plug, and plug holder on one wing. An oblong, suitably air-permeable and liquid-tight protective sheet has a sticky layer on one side and thereon a liquid-absorbing layer which is substantially smaller than half of the protective sheet and is located entirely within one half of the protective sheet when this is divided transversely and at a distance from the edges of the protective sheet. On top of said layers there are two protective pull sheets. A slit is arranged through the protective sheet, the sticky layer and one of the pull sheets from the end of the bandage farthest from the absorbent layer and up to a short distance from the absorbent layer.

4 Claims, 3 Drawing Figures

U.S. Patent  Jun. 30, 1981  4,275,721

VEIN CATHETER BANDAGE

The present invention relates to a vein catheter bandage.

A vein catheter usually consists of a thin hose, one end of which is pressed over the end of a thicker tube which has two lateral wings. The tube can either have a stop cock or can be closed and opened with a plug which, when it is not in the tube, is placed in a plug holder on one wing. The catheter hose is inserted with the help of a needle through the skin and into a patient's vein. It is then possible, through the tube, when the stop cock is open and there is no plug in the tube, to extract blood samples and inject medicine, anesthetics or nutrient solutions. Such a catheter may be kept in place in a patient for longer or shorter periods.

A major problem with putting in vein catheters is keeping the area around the incision sterile and free of blood, and at the same time keeping the catheter in place to avoid pulling and pushing movements of the hose. Up to now, to deal with the problem a combination of fastening means and loose compresses has been used which was changed as required once or twice a day. The use of several components made it more difficult to maintain sterility. Different people applying and changing these components often use different numbers of compresses and pieces of adhesive tape and apply them in different ways. Thus the anchoring of the catheter will vary in quality on different occasions.

There is no single bandage which keeps the incision both dry and free of bacteria. For catheter and drainage hoses without coupling tubes and stop cocks or plugs adjacent to the incision, various solutions have been suggested. U.S. Pat. No. 3,138,158 describes a three or four-armed fastener with a central portion with three holes. One of the holes is placed directly over the incision and the catheter hose is threaded up through the hole, down through a second hold and up through a third hole. Secure anchoring in the hose is to be achieved in this way. Another variant of the fastener is made as a rectangle with a central hole with teeth and a slit to the closest side edge. With the aid of the slit, the catheter hose is made to pass through the hole, and the teeth grip the hose and are presumed to hold it in place. There is no possibility of keeping the incision free of blood nor of absorbing injected nutrient solution, for example, which seeps out of the incision. It would be very difficult to combine this fastener with a compress. Also, the suggested fastener cannot be used for catheters with coupling tubes and stop cocks.

U.S. Pat. No. 3,683,911 suggests a bacteria-inhibiting anchoring device for a single catheter hose. The device consists of a bottom fastener from which a tube sticks up. The bottom of the fastener is coated with an adhesive combined with a germicidal substance. The same coating is applied to the inside of the tube. The tube and the fastener have a cut which makes it possible to place the device around the catheter hose. The adhesive on the fastener and in the tube makes it possible to hold the catheter hose in place and to prevent bacteria from entering the incision. There is no possibility of combining the device with an absorbent body, e.g. a compress, which will keep the incision free of blood, nor can the device be used with catheters with coupling tubes and stop cocks. It must also be very difficult to change such a fastening means and at the same time free the hose from the tube and the fastener from the patient's skin, without significant movement of the hose and irritation of the incision.

The purpose of the present invention is to achieve a bandage for vein catheters with tubular coupling pieces and associated plugs or stop cocks, which does not have the disadvantages mentioned and which is easy to apply and change and makes it easy to keep the area around the incision sterile.

The purpose according to the invention is achieved with a bandage consisting of an oblong, preferably air-permeable and liquid-tight protective sheet which has a sticky layer on one side and on top thereof a blood-absorbing layer which is substantially smaller than half of the protective layer and is located in its entirety within one half of the protective sheet when said sheet is divided transversely, and at a distance from the edges of the protective sheet, preferably a non-absorbent, liquid-permeable sheet which covers the absorbent layer, and on top of said layers, or on top of said layers and said sheets, two pull sheets protecting the sticky layer and together covering the entire surface of the protective sheet, said pull sheets extending from each short end of the protective sheet and meeting above the abosrbing layer of the non-absorbent sheet where their end portions form two gripping tabs, one of which is suitably folded back on itself and the other lying on top of it, a slit being arranged through the protective sheet, the sticky layer and the pull sheet from the end of the bandage which is farthest from the absorbent layer and extending to a short distance from the absorbent layer.

Suitably, the bandage is rectangular. The absorbent layer should be placed centrally on one half of the protective sheet and extend over, for example, a third of the width of the bandage and over, for example, a fifth of its length. The length of the bandage is suitably about 1.5 times its width.

In order to be able to use the bandage on a so-called Veneflon catheter, comprising a catheter hose, a tubular coupling member and two laterally directed wings and on the outer portion of one of the wings a plug holder with plug there is preferably arranged a tear perforation, square in shape, for example, for exposing a corresponding notch through the protective sheet, the sticky layer and one of the pull sheets, at one side edge of the bandage, placed so that when the notch is exposed by tearing out and the bandage has been freed from the pull sheets and been placed over a Veneflon catheter with the non-absorbent liquid-permeable sheet over the catheter incision and with the slit in the bandage on the catheter connecting tube, the catheter plug holder will lie in the notch obtained by tearing along the perforations.

When using the present bandage, the non-slitted pull sheet is removed first, and this is easily done by using the gripping tab on the pull sheet. The bandage, with the liquid-permeable, non-absorbent sheet and the absorbent body, is then placed over the incision, whereafter the second pull sheet is removed at the same time as the two flaps formed by the slit in the bandage, are applied over the wings of the catheter and on and beside the tubular coupling member. For Veneflon catheters, the tear perforation notch is exposed before the pull sheet is removed. The bandage is then applied in the described manner so that the notch will lie around the plug holder.

Bandages according to the invention are suitably packed in a sterile package together with a small compress of just the right size to lie under the catheter wings and prevent the catheter from irritating the patient's skin. When using the bandage, the package is first opened, and the sterile compress is placed under the catheter wings. The bandage is then applied in the manner described above.

The bandage according to the invention is very easy to apply and change. The catheter is held securely in place by virtue of the fact that the two fastener flaps hold down the catheter wings both below and above the catheter hole. It is especially important that the flaps be sufficiently long. The sticky portion around the absorbent body need not be so large however. The absorbent body is thus placed within one half of the bandage and the flaps can therefore be somewhat longer than half of the bandage.

The absorbent body with the liquid-permeable, non-absorbent sheet keeps the incision free of blood and any solutions injected through the catheter, which can seep out through the incision. The non-absorbent sheet helps keeping the incision dry and prevents the bandage from sticking to the incision as well.

The present invention makes it very easy to keep the area around a vein catheter sterile. This is due to several factors. It is used as a single-component bandage, preferably delivered in a sterile package together with a compress to be placed under the catheter wings. The bandage is easy to apply without extra fiddling with the bandage. The carrier material for the adhesive or sticky layer is also made as a barrier layer which is preferably air-permeable but liquid-proof. Bacteria-laden liquid cannot penetrate through the bandage and contaminate the incision. Furthermore, the slit in the bandage does not extend all the way to the absorbent body. Bacteria are thus also prevented from penetrating into the incision through contact between the absorbent body and the surrounding air or moisture.

The sheet layers in the bandage, i.e. the protective sheet, the liquid-permeable, non-absorbent sheet and the covering pull sheets, are made of suitable sheet materials such as tight plastic sheets or films, fiber materials such as non-woven fabric or paper, or woven fabric.

The material in the protective layer is preferably impregnated non-woven fabric such as rayon non-woven fabric, and the absorbent body can, for example, be made of spunbonded cellulose regenerate of suitable thickness.

The non-absorbent, liquid-permeable sheet can be, for example, a perforated plastic film, possibly aluminized, a synthetic-fiber non-woven material or the like. For the sticky layer an acrylate-based adhesive substance can be used. The pull sheets can be made of a suitable silicon-coated paper.

Figure 2:
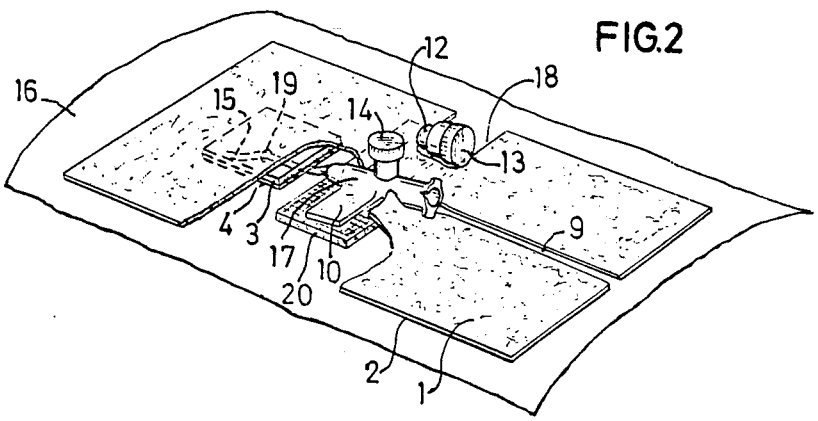
Figure 3:
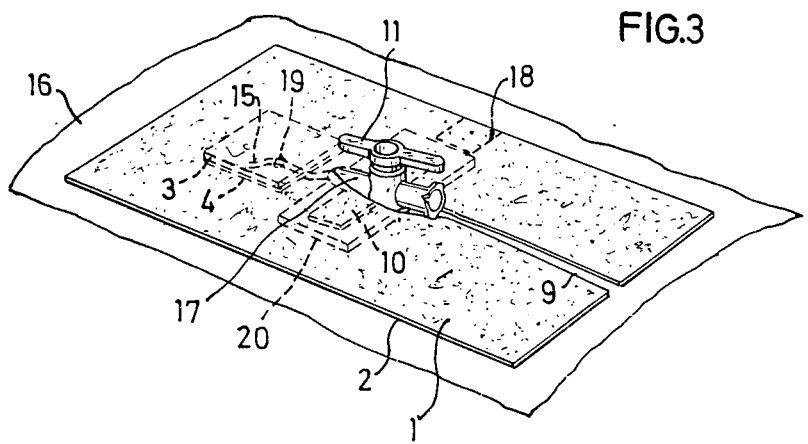

The invention is described in the following in more detail with reference to the accompanying drawings, in which FIG. 1 shows a partially cut-away perspective view of a suitable embodiment of the bandage according to the invention, FIG. 2 shows a partially cut-away view of this bandage applied onto a Veneflon catheter, and FIG. 3 shows a perspective view of the bandage applied to a catheter with a stop cock.

For the sake of clarity, the thickness of some of the layers as shown in the figures is exaggerated.

FIG. 1 shows a perspective view of an embodiment of the bandage according to the invention. The bandage consists of a rectangular, preferably waterproof and air-permeable protective sheet 1. The sheet is coated with a self-adhesive 2. Centrally, on one half of the sheet, there a square absorbent body 3 with a perforated, non-absorbent sheet 4 of equal size lying on top of it. The entire protective sheet with the layers on top of it is covered by two covering papers 5 and 6 which meet above the absorbent body and form two gripping tabs 7 and 8 with their end portions. One gripping tab 7 is folded back on itself and the other tab 8 lies over the folded tab. There is a square tear perforation 18 on the edge of the bandage.

The bandage described can be, for example, 95 mm long and 60 mm wide. The absorbent layer can be about 20×20 mm and be placed about 15 mm from the nearest short side and about 20 mm from each long side. The slit suitably extends centrally from the short side farthest away from the absorbent body up to about 5 mm from the absorbent body.

FIG. 2 shows the bandage applied over a Veneflon catheter. The catheter comprises a hose 15, a tubular coupling member 17 and two laterally extending wings 10. At the outer edge of one of the wings 10 there is a plug holder 12 and a plug 13. The plug 13 can be used to plug the tube 17. Above the tube 17, there is another opening with a plug 14. In the opening under the plug 14 there is a membrane which prevents blood from forcing its way up through the opening, but at the same time permits the introduction of medicines, for example, through the opening, at the same time as the tube 17 is open and blood, for example, is introduced therethrough. Under the wings there is a compress 20. The catheter hose 15, which is shown with a dashed line where it is not exposed, goes in through the patient's skin 16 at the incision 19. The perforated sheet 4 and the absorbent layer 3 are placed on top of the incision 19. The two flaps, which are created by the slit 9, are placed over the wings 10 and on either side of the tube 17.

FIG. 3 shows the bandage applied to a central catheter which has a tubular coupling member 17 and a stop cock 11 which can shut off and open the coupling member. In this case it is not necessary to tear out the square 18. Otherwise the bandage is applied to the same manner to this catheter as to the Veneflon catheter. The portions of the bandage and the catheter lying under the protective sheet 1 are drawn with dashed lines.

What I claim is:

1. Vein catheter bandage, characterized by an oblong, preferably air-permeable and liquid-tight protective sheet which has a sticky layer on one side and on top of that a liquid-absorbing layer which is substantially smaller than half of the protective sheet and is located in its entirety within one half of the protective sheet when said sheet is divided transversely, and at a distance from the edges of the protective sheet, preferably a non-absorbent, liquid-permeable sheet which covers the absorbent layer, the absorbent layer or in certain cases the non-absorbent sheet being intended, when the bandage is used, to lie against the incision of the vein catheter, and on top of said layers or on top of said layers and said sheet two covering pull sheets which together cover the entire surface of the protective sheet and extend from each end of the protective sheet, meeting above the absorbing layer of the non-absorbent sheet where their end portions form two gripping tabs, one folded back on itself and the other lying on top of the first, a slit being arranged through the protective sheet, the sticky layer and the pull sheet from the end of the bandage which is farthest from the absorbent layer and extending to a short distance from the absorbent layer.

2. Bandage according to claim 1, characterized in that the absorbent layer is placed centrally on one half of the protective sheet and covers approximately a third of the width of the bandage and approximately a fifth of its length.

3. Bandage according to claim 1 or 2, which is intended for a Veneflon catheter with connecting tube, two laterally extending wings and a plug holder with plug on one wing, characterized in that a suitably square tear perforation, intended to expose a corresponding notch, is arranged through the protective sheet, the sticky layer and the pull sheet at one side edge of the bandage, placed so that when the notch has been exposed by tearing out and the bandage has been placed over a Veneflon catheter with the non-absorbent, liquid-permeable sheet over the incision for the catheter and with the slit in the bandage on the connecting tube of the catheter, the plug holder of the Veneflon catheter will lie in the notch obtained by the tear perforation.

4. Bandage according to any one of claims 1-3, characterized in that its length is about 1.5 times its width.

* * * * *